US010369182B2

(12) United States Patent
Cohen

(10) Patent No.: US 10,369,182 B2
(45) Date of Patent: Aug. 6, 2019

(54) COMPOSITIONS AND METHODS FOR TREATING INSOMNIA AND OTHER SLEEP RELATED DISORDERS

(71) Applicant: Script Essentials, LLC, Broomfield, CO (US)

(72) Inventor: Suzy Cohen, Broomfield, CO (US)

(73) Assignee: SCRIPT ESSENTIALS, LLC, Broomfield, CO (US)

( * ) Notice: Subject to any disclaimer, the term of this patent is extended or adjusted under 35 U.S.C. 154(b) by 0 days.

(21) Appl. No.: 16/026,541

(22) Filed: Jul. 3, 2018

(65) Prior Publication Data

US 2019/0000907 A1 Jan. 3, 2019

Related U.S. Application Data

(60) Provisional application No. 62/528,272, filed on Jul. 3, 2017.

(51) Int. Cl.
| | | |
|---|---|---|
| *A61K 36/00* | (2006.01) | |
| *A61K 36/53* | (2006.01) | |
| *A61K 31/675* | (2006.01) | |
| *A61K 31/198* | (2006.01) | |
| *A61K 31/197* | (2006.01) | |
| *A61K 31/405* | (2006.01) | |
| *A61K 31/4045* | (2006.01) | |
| *A61K 36/185* | (2006.01) | |
| *A61K 9/48* | (2006.01) | |
| *A61K 9/20* | (2006.01) | |
| *A23L 33/105* | (2016.01) | |
| *A23L 33/15* | (2016.01) | |
| *A23L 33/175* | (2016.01) | |
| *A61K 36/28* | (2006.01) | |
| *A61K 9/00* | (2006.01) | |
| *A61K 31/00* | (2006.01) | |
| *A61K 31/4415* | (2006.01) | |
| *A23L 33/10* | (2016.01) | |

(52) U.S. Cl.
CPC .............. *A61K 36/53* (2013.01); *A23L 33/10* (2016.08); *A23L 33/105* (2016.08); *A23L 33/15* (2016.08); *A23L 33/175* (2016.08); *A61K 9/0053* (2013.01); *A61K 9/20* (2013.01); *A61K 9/2068* (2013.01); *A61K 9/48* (2013.01); *A61K 9/4875* (2013.01); *A61K 31/00* (2013.01); *A61K 31/197* (2013.01); *A61K 31/198* (2013.01); *A61K 31/405* (2013.01); *A61K 31/4045* (2013.01); *A61K 31/4415* (2013.01); *A61K 31/675* (2013.01); *A61K 36/185* (2013.01); *A61K 36/28* (2013.01); *A23V 2002/00* (2013.01)

(58) Field of Classification Search
CPC ............................ A61K 36/00; A61K 31/195
See application file for complete search history.

(56) References Cited

U.S. PATENT DOCUMENTS

2008/0044499 A1\* 2/2008 Ozeki .................. A61K 31/045
424/730

\* cited by examiner

*Primary Examiner* — Rosanne Kosson
(74) *Attorney, Agent, or Firm* — Lewis Brisbois Bisgaard & Smith LLP

(57) ABSTRACT

The present disclosure is a composition, a method of making the composition and method of using such composition preferably in the form of a dietary supplement that, when administered, is capable of treating insomnia and other sleep-related disorders. The unique combination of the composition is preferably administered orally. The composition is preferably comprised of at least vitamin B6, chamomile extract, passionflower extract, lemon balm extract, L-Theanine, GABA, 5-Hydroxytryptophan, and melatonin, in predetermined amounts. The composition can further comprise a palliative agent, and can be provided in the form of a capsule, powder, liquid or tablet.

15 Claims, No Drawings

COMPOSITIONS AND METHODS FOR TREATING INSOMNIA AND OTHER SLEEP RELATED DISORDERS

CROSS-REFERENCE TO RELATED APPLICATIONS

This application claims priority to and the benefit under 35 U.S.C. § 119(e) to U.S. Provisional Patent Application Ser. No. 62/528,272, filed on Jul. 3, 2017, which is incorporated by reference herein in its entirety.

FIELD OF THE INVENTION

The present disclosure is directed to novel compounds, which may be administered in the form of a dietary supplement, and which are beneficial in treating insomnia and sleep-related disorders. The present disclosure also relates to methods for formulating and administering the same.

BACKGROUND OF THE INVENTION

The brain is critically involved in regulating sleep and maintaining regular sleep cycles. The pineal gland of the brain is responsible for secreting melatonin. Melatonin is a hormone that helps to control sleep and wake cycles, also known as circadian rhythms.

Despite recommended levels exceeding seven hours of sleep per night, many adults suffer from chronic sleep deprivation, irregular sleep patterns and other sleep disorders. In addition, nearly 60 million Americans suffer from chronic insomnia. Approximately 90% of people will acquire transient insomnia, also known as adjustment sleep disorder, at some point in their lives.

Insomnia disproportionately affects women and people over the age of 65. Insomnia often causes complications such as chronic fatigue, higher risk of stroke, heart attack, irritability, substance abuse, depression and obesity. Insomnia is not only a state of sleep loss, but a disorder of hyperarousal, which often remains present day and night. Physiological and psychological factors that contribute to the onset of insomnia include but are not limited to: stressful events, thyroid conditions, anxious or depressed personality traits, age-related sleep homeostasis, weakening mechanisms, perimenopause and menopause. Chronic insomnia may result in impaired occupational performance, may contribute to adverse health conditions, and often affects quality of life.

These and other problems are addressed by the compositions and methods described in detail below.

SUMMARY OF THE INVENTION

The present disclosure relates to compositions, preferably in the form of a dietary supplement, which addresses the sleep disorders described above, improves restorative sleep and normal circadian rhythms, and otherwise addresses a long-felt but unresolved need experienced by millions of people suffering from insomnia and impaired sleep.

In varying embodiments described herein, the present disclosure relates to a composition that is capable of treating insomnia, impaired sleep and other sleep-related disorders. Certain elements of the novel compositions and methods for formulating the same are described in varying levels of detail herein.

In addition to the problems associated with sleep disorders and abnormalities described herein, insomniacs are also more susceptible to numerous health conditions, including heart disease, heart attack, heart failure, irregular heartbeat, high blood pressure, stroke, and diabetes. The compositions and methods described herein may also provide benefits to a person's overall health and well-being. Insomnia may also cause or contribute to increased traffic accidents, weight gain, impaired judgment, occupational hazards, decreased libido, depression, decreased memory, and diminished cognitive ability.

Through experimentation, it has been found that including various nutrients and herbs, such as lemon balm extract, passionflower extract and 5-HTP in the form of a dietary supplement can be beneficial to people who have conditions that adversely affect their sleep. More particularly, people who are deficient in melatonin and 5-HTP frequently suffer from insomnia. Melatonin has been shown to increase sleep latency. Therefore, it would be desirable to include melatonin and 5-HTP in a dietary supplement in order to positively influence sleep patterns.

Through experimentation, the Applicant has found that compositions containing a highly absorbable form of vitamin B6 can help a person with sleep disorders (poor sleep duration, fitful sleep, inability to achieve REM sleep, inability to achieve 4 phases of sleep, and sleep latency). In addition, dietary supplements containing chamomile extract have been shown to reestablish normal circadian rhythms, improve restorative sleep, and reduce sleep latency. After oral supplementation with the herbal extract of chamomile, the amount and quality of sleep have been found to normalize. Therefore, it would be desirable to include appropriate amounts of chamomile or equivalent extract in a dietary supplement in order to positively influence sleep patterns.

GABA has also been found through experimentation to be beneficial to treating sleep disorders. GABA supplementation is particularly beneficial to individuals who suffer from insomnia because activation of GABA receptors favors sleep. Therefore, providing a composition that also comprises appropriate levels of GABA can also be beneficial. Other nutrients and compounds can provide further benefits to the brain of the human body, and are described in greater detail herein.

Methods for formulating and administering these novel compositions are also disclosed herein.

The unique combination of each composition described herein is preferably administered orally in the form of a capsule. The unique combination has synergistic advantages over previously known compositions. As disclosed in more detail in the Detailed Description, the present invention provides compositions, methods for treating insomnia and other sleep disorders, and methods for forming the compound.

The composition is preferably comprised of a unique and novel formulation in predetermined amounts, and further provides benefits previously unexpected. In addition to other health benefits described herein, the composition:
  enhances the production of melatonin
  provides for all 4 phases of sleep, including REM
  provides for healthy circadian rhythms
  assists the human body in optimizing metabolism
  improves restorative sleep patterns
  reduces sleep latency
  improves cognitive ability In certain embodiments, the composition provides additional nutrients necessary for management of anxiety and stress, reduction of nightmares, and improvement of memory retention during waking hours.

In a preferred embodiment, the composition is comprised of at least predetermined amounts of Vitamin B6 (P5P), L-theanine, GABA, 5-HTP, melatonin, and a blend of herbal components, by way of example including but not limited to, chamomile extract, passionflower extract, and lemon balm extract or combinations/sub-combinations thereof. These ingredients may be included, in whole or in part with the composition, and promote regular, restorative sleep, and as described in detail herein.

More particularly, a preferred embodiment of the present disclosure comprises the following, with variability in dosages listed below:

1) Vitamin B6—between about 1 mg and about 100 mg; in a most preferred embodiment comprising P5P (pyridoxal-5-phosphate), the biologically active metabolite of B6, in similar quantities.

2) L-Theanine—between about 10 mg and about 300 mg;

3) GABA—between about 20 mg and about 1000 mg;

4) 5-Hydroxytryptophan—between about 1 mg and about 150 mg;

5) Melatonin—between about 0.3 mg and about 5 mg.

In some embodiments, the proprietary blend may contain any one of the following additional ingredients, alone or in any combination:

6) Chamomile Extract—between about 100 mg and about 500 mg;

7) Passionflower Extract—between about 10 mg and about 300 mg; and

8) Lemon Balm Extract—between about 25 mg and about 250 mg.

In one embodiment, the composition is provided as a dietary supplement. In another embodiment, the composition is administered in the form of a capsule. In yet another embodiment, the composition is administered in the form of a gummy chew, tablet, powder or liquid extract. In further embodiments, the composition comprises one or more palatability agents to favorably alter the taste of the composition for human consumption.

These and other advantages will be apparent from the disclosure of the invention(s) contained herein. The above-described embodiments, objectives, and configurations are neither complete nor exhaustive. The Summary of the Invention is neither intended nor should it be construed as being representative of the full extent and scope of the present invention.

References made herein to "the present invention", "the present disclosure" or aspects thereof should be understood to mean certain embodiments of the present invention and should not necessarily be construed as limiting all embodiments to a particular description. The present invention is set forth in various levels of detail in the Summary of the Invention and the Detailed Description, and no limitation as to the scope of the present invention is intended by either the inclusion or non-inclusion of elements in this Summary of the Invention. Additional aspects of the present invention will become more readily apparent from the Detailed Description and appended claims.

DETAILED DESCRIPTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

As used herein, the phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being modified in all instances by the term "about".

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials, or acts and the equivalents thereof shall include all those described in the summary of the invention, brief description of the drawings, detailed description, abstract, and claims themselves.

Composition:

Vitamin B6

In a preferred embodiment, the composition is comprised of vitamin B6. In a most preferred embodiment, the composition is comprised of a pre-determined amount of the activated (metabolically active) form of vitamin B6 known as pyridoxal-5-phosphate, abbreviated as P5P. It has been found from experimentation that this form of vitamin B6 is optimal for human absorption in treating insomnia and other sleep disorders. Vitamin B6 administered in the quantities described herein has also been found to help improve the conversion of 5-HTP into melatonin, and at the same time remove a common deficiency in vitamin B6, which can lead to diminished GABA synthesis. A deficiency of vitamin B6 can also cause or exacerbate insomnia, nerve pain, problems with carbohydrate metabolism, dermatitis with cheilosis, microcytic anemia, electroencephalographic abnormalities, glossitis, depression and confusion, and weakened immune function. Individuals at risk for vitamin B6 deficiency include those suffering from end-stage renal diseases, chronic renal insufficiency, and other kidney diseases, alcohol dependency, and malabsorption syndromes, such as ulcerative colitis, celiac disease, and Crohn's disease. Long-term use of some medications, including antiepileptic drugs, contribute to vitamin B6 deficiency, as can certain genetic diseases, such as homocystinuria, further amplifying these concerns.

In a preferred embodiment, the composition comprises from about 1 mg to 100 mg of Vitamin B6, preferably as P5P. In a most preferred embodiment, the composition comprises about 1 mg to about 20 mg of P5P. In alternate embodiments, one or more additional water-soluble vitamins are included or substituted for vitamin B6.

L-Theanine

L-theanine is a water-soluble amino acid found in tea, and to a lesser extent in mushrooms. It is used to treat anxiety and high blood pressure, to improve concentration and focus, to reduce the risk of stroke, to prevent Alzheimer's disease, and for increasing the effectiveness of cancer drugs. L-theanine's anti-anxiety benefits have also been shown to prevent nightmares, increasing restful sleep.

L-theanine has further been found to neutralize the negative effects of caffeine. Increasing evidence indicates L-theanine can induce pre-sleep relaxation, which can be very effective against insomnia. In addition, research shows that L-theanine can improve the quality of sleep by helping individuals to recover from exhaustion, and awaken feeling refreshed. Evidence from human electroencephalograph (EEG) studies show its direct effect on the brain. L-theanine increases activity in the alpha frequency band, indicating that it relaxes the mind without inducing drowsiness.

L-theanine can penetrate the blood-brain barrier to positively affect brain chemistry, with mood-modulating effects. L-theanine has been proven to affect levels of amino acids, which in turn increases serotonin (which ultimately produces melatonin) and other neurotransmitters in the brain.

Accumulating research indicates that L-theanine may have positive effects on the liver, particularly for individuals who consume alcohol. It works to restore the liver's antioxidant and detoxifier known as glutathione.

In a preferred embodiment, the composition comprises from about 10 mg to 300 mg of L-theanine. In a most preferred embodiment, the composition comprises about 50 mg to about 150 mg of L-theanine.

GABA

Gamma-Aminobutyric Acid or "GABA" is a neurotransmitter that blocks impulses between nerve cells in the brain. The human body produces GABA from the consumption of glutamate. Low levels of GABA may be linked to insomnia, anxiety, depression, epilepsy, severe premenstrual syndrome, chronic pain, attention deficit hyperactivity disorder (ADHD), and retention of fat. Limited studies have shown a possible link between GABA and lowered blood pressure. It has been shown through experimentation that activation of GABA receptors favors sleep, especially in the quantities described for administration herein.

Supplementation with GABA has also been found to help prevent nightmares, increasing restful sleep. Studies have indicated that healthy people with insomnia often have GABA deficiencies and, as mentioned above, deficiency in vitamin B6 can lead to diminished GABA synthesis. Increasing evidence indicates that individuals who supplement with GABA fall asleep faster, have longer quality sleep time, and have reported feeling more energized in the morning.

In a preferred embodiment, the composition comprises from about 20 mg to 1000 mg of GABA. In a most preferred embodiment, the composition comprises about 75 mg to about 200 mg of GABA.

5-Hydroxytryptophan

5-Hydroxytryptophan (also known as 5-HTP or oxitriptan) is extracted from the seed of griffonia simplicifolia, a climbing vine found in west and central Africa. 5-HTP is a naturally occurring amino acid and chemical precursor, as well as a metabolic intermediate in the biosynthesis of the neurotransmitter serotonin. Serotonin has been found to improve, over time, the way we sleep, as it breaks down into melatonin. Further, serotonin has been found to positively affect appetite, temperature, sexual behavior, and pain sensation. Since 5-HTP increases the synthesis of serotonin, it is often used for treatment of various diseases.

Increasing evidence indicates that 5-HTP in the amounts described herein is helpful in preventing depression, fibromyalgia, insomnia, migraines and tension headaches, obesity, premenstrual syndrome (PMS), premenstrual dysphoric disorder (PMDD), attention deficithyperactivity disorder (ADHD), seizure disorders, and Parkinson's disease.

In a preferred embodiment, the composition comprises from about 1 mg to 150 mg of 5-HTP. In a most preferred embodiment, the composition comprises about 25 mg to about 75 mg of 5-HTP (derived from griffonia simplicifolia extract, a plant native to West Africa).

Melatonin

Melatonin (N-acetyl-5-methoxytryptamine) is a hormone that is produced by the pineal gland (located above the middle of the brain) to regulate sleep and wakefulness. It is involved in the synchronization of the circadian rhythms, including sleep-wake timing, blood pressure regulation, and many others. Melatonin is an antioxidant with a role in the protection of nuclear and mitochondrial DNA.

In addition to its use in treating individuals with sleep disorders, accumulating evidence indicates it may be useful for treating jet lag and for individuals who have professions that require them to work unusual hours, tinnitus (ringing in the ears), cluster headaches, pre- and post-operative anxiety, gallstones, and protection against radiation-induced cellular damage.

In a preferred embodiment, the composition comprises from about 0.3 mg to 5 mg of melatonin. In a most preferred embodiment, the composition comprises about 0.5 mg to about 1.5 mg of melatonin.

Chamomile

Chamomile (*Chamomilla recutita* or *Chamaemelum nobile*), a member of the daisy family, is an ancient medicinal herb containing terpenoids and flavonoids. It has been used for thousands of years as an anti-inflammatory, antioxidant, mild astringent and healing medicine. Today, chamomile is used to treat a variety of human ailments including hay fever, premenstrual syndrome (PMS) and premenstrual dysphoric disorder (PMDD), inflammation, muscle spasms, insomnia, ulcers, wounds, gastrointestinal disorders, rheumatic pain, and hemorrhoids.

There are a host of other conditions for which chamomile is used as traditional treatment, including but not limited to, treatment of skin inflammations, poison ivy, eczema, skin irritations, rheumatic pain, hemorrhoids, mastitis, diaper rash, cracked nipples, and chicken pox. Chamomile has been frequently used as a mild sedative to reduce anxiety and to treat nightmares. Chamomile may also be effective in arthritis, back pain, and non-menstrual abdominal cramps.

In a preferred embodiment, the composition comprises from about 100 mg to 500 mg of chamomile extract. In a most preferred embodiment, the composition comprises about 250 mg to about 350 mg of chamomile extract (standardized to 0.4% flavonoids). In alternate embodiments, one or more additional herbal extracts are included or substituted for chamomile extract.

Passionflower Extract

Passionflower (*passiflora incarnata*), also known as maypop or purple passion flower, is a creeping perennial vine that is a known botanical in Chinese and Ayurvedic medicine. Increasing evidence indicates its value in treating anxiety as well as its benefits in prescription medications. Passionflower extract's anti-anxiety benefits may help to prevent nightmares. It has been used to treat gastrointestinal upset, symptoms related to narcotic drug withdrawal, seizures, asthma, symptoms of menopause, attention deficit hyperactivity disorder (ADHD), nervousness, palpitations, irregular heartbeat, high blood pressure, fibromyalgia, and pain relief. Passionflower extract has also been utilized as an application to the skin for hemorrhoids, burns, and inflammation.

In a preferred embodiment, the composition comprises from about 10 mg to about 300 mg passionflower extract. In a most preferred embodiment, the composition comprises about 50 mg to about 150 mg passionflower extract (standardized to 3.5% flavonoids).

Lemon Balm

Lemon balm (Melissa officinalis), is a perennial herbaceous plant in the mint family native to south-central Europe, the Mediterranean Basin, Iran, and Central Asia. It has been utilized in traditional medicine to improve appetite, reduce stress and anxiety, to treat venomous insect bites and stings, and ease pain and discomfort from indigestion. Recent studies indicate it may be useful in healing cold sores caused by herpes simplex virus (HSV). Its antibacterial properties show promise for its use in fighting infections caused by HIV, Listeria monocytogenes and Staphylococcus aureus. Increasing evidence indicates value in improving cognitive function and decreasing agitation in people with Alzheimer's disease.

In a preferred embodiment, the composition comprises from about 25 mg to 250 mg of lemon balm extract. In a most preferred embodiment, the composition comprises about 75 mg to about 150 mg of lemon balm extract (standardized to 3% resmarinic acid).

Absent Elements

In addition, the composition of a preferred embodiment is substantially free of the following common allergens: gluten, wheat, eggs, peanuts, tree nuts, dairy, sugar, corn, soy, yeast, fish and shellfish. The composition preferably does not contain artificial colors, flavors, or preservatives, and is free from magnesium stearate (a common lubricant used in the manufacture of pharmaceuticals and dietary supplements).

Additional Elements

In varying embodiments, the composition can further comprise variances in regards to encapsulation, sublinguals, or powder formulations. According to certain embodiments, the compositions described herein can further be provided with one or more palatability agents. These palatability agents serve to add flavor to the composition so that an effective dosage is easier to be ingested. It is within the scope of the present invention that any safe, flavor enhancing palatability agent can be used in a composition of the present invention. Particularly suitable palatability agents for use in the composition of the present invention include, but are not limited to, plant oils, plant hydrolysates, yeast, yeast hydrolysates, and combinations thereof.

Methods

An aspect of the invention is a method to treat sleep-related disorders with a composition comprising: about 1 mg to about 20 mg of PSP; about 50 mg to about 150 mg of L-theanine; about 75 mg to about 200 mg of GABA; about 25 mg to about 75 mg of 5-HTP; about 0.5 mg to about 1.5 mg of melatonin; about 250 mg to about 350 mg of chamomile extract; about 50 mg to about 150 mg passionflower extract; and about 75 mg to about 150 mg of lemon balm extract. According to varying embodiments, the patient is preferably treated by providing an effective amount of the composition. By way of example, between 1 and 3 capsules of the composition can be provided to a patient per day, in some embodiments 2 capsules per day. The capsules can be taken by the patient daily, preferably in the evening 30 to 90 minutes before bed.

Another aspect of the invention is a method to prepare a composition to treat insomnia. The method comprises providing proportional amounts of each material such that the resulting composition results in between about 1 mg and about 100 mg of vitamin B6; between about 10 mg and about 300 mg of L-Theanine; between about 20 mg and about 1000 mg of GABA; between about 1 mg and about 150 mg of 5-Hydroxytryptophan; and between about 0.3 mg and about 5 mg of melatonin. In some embodiments, the blend can contain any one of the following ingredients, alone or in any combination: between about 100 mg and about 500 mg of chamomile extract; between about 10 mg and about 300 mg of passionflower extract; and between about 25 mg and about 250 mg of lemon balm extract. The components are mixed, and then can be provided to a delivery device (for example, a capsule).

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

Ranges have been discussed and used within the forgoing description. One skilled in the art would understand that any sub-range within the stated range would be suitable, as would any number within the broad range, without deviating from the invention.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

What is claimed is:

1. A composition for treating insomnia, comprising:
   (a) between about 1 to 100 mg of vitamin B6;
   (b) between about 10 to 300 mg of L-Theanine;
   (c) between about 20 to 1000 mg of y-aminobutyric acid (GABA);
   (d) between about 1 to 150 mg of 5-Hydroxytryptophan;
   (e) between about 0.3 to 5 mg of Melatonin,
   (f) between about 100 to 500 mg of chamomile extract:
   (g) between about 10 to 300 mg of passionflower extract; and
   (h) between about 25 to 250 mg of lemon balm extract.

2. The composition of claim 1, wherein the composition is provided as a dietary supplement.

3. The composition of claim 1, wherein the composition is administered orally in the form of a capsule.

4. The composition of claim 1, wherein the composition is administered orally in the form of a tablet.

5. The composition of claim 1, wherein the composition is substantially free of at least one of gluten, wheat, eggs, peanuts, tree nuts, dairy, sugar, corn, soy, yeast, artificial colors, preservatives, fish and shellfish.

6. The composition of claim 1, further comprising at least one palatability agent, and wherein the palatability agent is selected from the group consisting of a plant oil, a plant hydrolysate, yeast, a yeast hydrolysate, and combinations thereof.

7. The composition of claim 1, wherein the vitamin B6 is pyridoxal-5-phosphate, and comprises about 5 mg of pyridoxal-5-phosphate.

8. The composition of claim 1, wherein the composition comprises about 100 mg of L-Theanine.

9. The composition of claim 1, wherein the composition comprises about 100 mg of GABA.

10. The composition of claim 1, wherein the composition comprises about 50 mg of 5-HTP.

11. The composition of claim 1, wherein the composition comprises about 1 mg of melatonin.

12. The composition of claim 1, wherein the chamomile is standardized to 0.4% flavonoids, and wherein the composition comprises about 300 mg of chamomile extract.

13. The composition of claim 1, wherein the passionflower extract is standardized to 3.5% flavonoids, and wherein the composition comprises about 100 mg of passionflower extract.

14. The composition of claim 1, wherein the lemon balm extract is standardized to 3% resmarinic acid, and wherein the composition comprises about 100 mg of lemon balm extract.

15. A method for treating sleep-related disorders by administering to a patient in need thereof a therapeutically effective amount of the composition of claim 1.

* * * * *